United States Patent
Abrams (10) Patent No.: US 7,871,369 B2
(45) Date of Patent: *Jan. 18, 2011

(54) CARDIAC SLEEVE APPARATUS, SYSTEM AND METHOD OF USE

(75) Inventor: Robert M. Abrams, Los Gatos, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 121 days.

This patent is subject to a terminal disclaimer.

(21) Appl. No.: 12/415,583

(22) Filed: Mar. 31, 2009

(65) Prior Publication Data

US 2009/0187064 A1 Jul. 23, 2009

Related U.S. Application Data

(63) Continuation of application No. 11/215,666, filed on Aug. 29, 2005, now Pat. No. 7,524,282.

(51) Int. Cl.
*A61F 13/00* (2006.01)

(52) U.S. Cl. .................................................. 600/37

(58) Field of Classification Search .............. 600/16, 600/17, 37; 607/129; 623/3.1, 3.16, 3.29, 623/3.11, 3.17, 3.21
See application file for complete search history.

(56) References Cited

U.S. PATENT DOCUMENTS

| | | | |
|---|---|---|---|
| 5,409,460 A | 4/1995 | Krumme | |
| 5,824,045 A | 10/1998 | Alt | |
| 5,843,117 A | 12/1998 | Alt et al. | |
| 5,855,600 A | 1/1999 | Alt | |
| 5,871,437 A | 2/1999 | Alt | |
| 6,027,510 A | 2/2000 | Alt | |
| 6,053,873 A | 4/2000 | Govari et al. | |
| 6,099,561 A | 8/2000 | Alt | |
| 6,106,473 A | 8/2000 | Violante et al. | |
| 6,159,142 A | 12/2000 | Alt | |
| 6,159,237 A | 12/2000 | Alt et al. | |
| 6,231,516 B1 | 5/2001 | Keilman et al. | |
| 6,245,104 B1 | 6/2001 | Alt | |
| 6,251,134 B1 | 6/2001 | Alt et al. | |
| 6,280,385 B1 | 8/2001 | Melzer et al. | |
| 6,304,769 B1 | 10/2001 | Arenson et al. | |
| 6,387,121 B1 | 5/2002 | Alt | |
| 6,398,805 B1 | 6/2002 | Alt | |

(Continued)

FOREIGN PATENT DOCUMENTS

WO WO 02/43617 6/2002

(Continued)

OTHER PUBLICATIONS

International Search Report. Dec. 28, 2006. 4 pgs.

(Continued)

*Primary Examiner*—Niketa I Patel
*Assistant Examiner*—Rex Holmes
(74) *Attorney, Agent, or Firm*—Brooks, Cameron & Huebsch, PLLC (57) ABSTRACT

Cardiac assist sleeve and methods for using and making the cardiac assist sleeve that includes first elongate strips and second elongate strips of memory alloy that change shape to change a volume of cardiac assist sleeve.

12 Claims, 7 Drawing Sheets

U.S. PATENT DOCUMENTS

| | | |
|---|---|---|
| 6,416,540 B1 | 7/2002 | Mathur |
| 6,425,856 B1 | 7/2002 | Shapland et al. |
| 6,463,317 B1 | 10/2002 | Kucharczyk et al. |
| 6,478,815 B1 | 11/2002 | Alt |
| 6,511,325 B1 | 1/2003 | Lalka et al. |
| 6,516,213 B1 | 2/2003 | Nevo |
| 6,574,497 B1 | 6/2003 | Pacetti |
| 6,585,660 B2 | 7/2003 | Dorando et al. |
| 6,585,755 B2 | 7/2003 | Jackson et al. |
| 6,585,763 B1 | 7/2003 | Keilman et al. |
| 6,628,980 B2 | 9/2003 | Atalar et al. |
| 6,652,540 B1 | 11/2003 | Cole et al. |
| 6,663,570 B2 | 12/2003 | Mott et al. |
| 6,668,197 B1 | 12/2003 | Habib et al. |
| 6,673,104 B2 | 1/2004 | Barry |
| 6,676,694 B1 | 1/2004 | Weiss |
| 6,702,847 B2 | 3/2004 | DiCarlo |
| 6,711,429 B1 | 3/2004 | Gilboa et al. |
| 6,711,440 B2 | 3/2004 | Deal et al. |
| 6,712,844 B2 | 3/2004 | Pacetti |
| 6,716,237 B1 | 4/2004 | Alt |
| 6,718,203 B2 | 4/2004 | Weiner et al. |
| 6,718,207 B2 | 4/2004 | Connelly |
| 6,725,092 B2 | 4/2004 | MacDonald et al. |
| 6,731,979 B2 | 5/2004 | MacDonald |
| 6,757,566 B2 | 6/2004 | Weiner et al. |
| 6,760,628 B2 | 7/2004 | Weiner et al. |
| 6,763,268 B2 | 7/2004 | MacDonald et al. |
| 6,765,144 B1 | 7/2004 | Wang et al. |
| 6,767,360 B1 | 7/2004 | Alt et al. |
| 6,778,856 B2 | 8/2004 | Connelly et al. |
| 6,782,284 B1 | 8/2004 | Subramanyan et al. |
| 6,786,904 B2 | 9/2004 | Doscher et al. |
| 6,795,730 B2 | 9/2004 | Connelly et al. |
| 6,795,736 B2 | 9/2004 | Connelly et al. |
| 6,799,069 B2 | 9/2004 | Weiner et al. |
| 6,802,811 B1 | 10/2004 | Slepian |
| 6,802,857 B1 | 10/2004 | Walsh et al. |
| 6,808,535 B1 | 10/2004 | Jordan |
| 6,819,954 B2 | 11/2004 | Connelly |
| 6,819,958 B2 | 11/2004 | Weiner et al. |
| 6,829,509 B1 | 12/2004 | MacDonald et al. |
| 6,844,492 B1 | 1/2005 | Wang et al. |
| 6,845,266 B2 | 1/2005 | Weiner et al. |
| 6,847,837 B1 | 1/2005 | Melzer et al. |
| 6,850,804 B2 | 2/2005 | Eggers et al. |
| 6,850,805 B2 | 2/2005 | Connelly et al. |
| 6,875,180 B2 | 4/2005 | Weiner et al. |
| 6,884,234 B2 | 4/2005 | Aita et al. |
| 6,892,090 B2 | 5/2005 | Verard et al. |
| 6,898,454 B2 | 5/2005 | Atalar et al. |
| 6,901,290 B2 | 5/2005 | Foster et al. |
| 6,908,468 B2 | 6/2005 | Daum |
| 6,925,322 B2 | 8/2005 | Helfer et al. |
| 6,925,328 B2 | 8/2005 | Foster et al. |
| 6,954,674 B2 | 10/2005 | Connelly |
| 6,957,098 B1 | 10/2005 | Hyde et al. |
| 2001/0031919 A1 | 10/2001 | Strommer et al. |
| 2001/0031920 A1 | 10/2001 | Kaufman et al. |
| 2002/0019660 A1 | 2/2002 | Gianotti et al. |
| 2002/0026230 A1 | 2/2002 | Moll et al. |
| 2002/0040815 A1 | 4/2002 | Van Vaals |
| 2002/0045816 A1 | 4/2002 | Atalar et al. |
| 2002/0049375 A1 | 4/2002 | Strommer et al. |
| 2002/0082679 A1 | 6/2002 | Sirhan et al. |
| 2002/0082685 A1 | 6/2002 | Sirhan et al. |
| 2002/0137014 A1 | 9/2002 | Anderson et al. |
| 2002/0173724 A1 | 11/2002 | Dorando et al. |
| 2002/0188345 A1 | 12/2002 | Pacetti |
| 2003/0004562 A1 | 1/2003 | DiCarlo |
| 2003/0004563 A1 | 1/2003 | Jackson et al. |
| 2003/0074049 A1 | 4/2003 | Hoganson et al. |
| 2003/0083579 A1 | 5/2003 | Aita et al. |
| 2003/0087244 A1 | 5/2003 | McCarthy |
| 2003/0088178 A1 | 5/2003 | Owens et al. |
| 2003/0088308 A1 | 5/2003 | Scheuermann et al. |
| 2003/0092013 A1 | 5/2003 | McCarthy et al. |
| 2003/0096248 A1 | 5/2003 | McCarthy et al. |
| 2003/0099957 A1 | 5/2003 | McCarthy |
| 2003/0100830 A1 | 5/2003 | Zhong et al. |
| 2003/0105069 A1 | 6/2003 | Robinson et al. |
| 2003/0139739 A1 | 7/2003 | Doscher et al. |
| 2003/0143544 A1 | 7/2003 | McCarthy |
| 2003/0144728 A1 | 7/2003 | Scheuermann et al. |
| 2003/0153949 A1 | 8/2003 | Lau et al. |
| 2003/0163052 A1 | 8/2003 | Mott et al. |
| 2003/0187335 A1 | 10/2003 | McCarthy |
| 2003/0199747 A1 | 10/2003 | Michlitsch et al. |
| 2003/0212448 A1 | 11/2003 | Smith |
| 2004/0010304 A1 | 1/2004 | Weber et al. |
| 2004/0019376 A1 | 1/2004 | Alt |
| 2004/0030379 A1 | 2/2004 | Hamm et al. |
| 2004/0034300 A1 | 2/2004 | Verard et al. |
| 2004/0038406 A1 | 2/2004 | Unger et al. |
| 2004/0039438 A1 | 2/2004 | Alt |
| 2004/0044397 A1 | 3/2004 | Stinson |
| 2004/0059280 A1 | 3/2004 | Makower et al. |
| 2004/0082866 A1 | 4/2004 | Mott et al. |
| 2004/0091603 A1 | 5/2004 | Priewe |
| 2004/0093075 A1 | 5/2004 | Kuehne |
| 2004/0097804 A1 | 5/2004 | Sobe |
| 2004/0097805 A1 | 5/2004 | Verard et al. |
| 2004/0098093 A1 | 5/2004 | DiCarlo |
| 2004/0111016 A1 | 6/2004 | Casscells, III et al. |
| 2004/0116997 A1 | 6/2004 | Taylor et al. |
| 2004/0117007 A1 | 6/2004 | Whitborne et al. |
| 2004/0122494 A1 | 6/2004 | Eggers et al. |
| 2004/0133069 A1 | 7/2004 | Shapland et al. |
| 2004/0143154 A1 | 7/2004 | Lau et al. |
| 2004/0143180 A1 | 7/2004 | Zhong et al. |
| 2004/0158310 A1 | 8/2004 | Weber et al. |
| 2004/0186377 A1 | 9/2004 | Zhong et al. |
| 2004/0210289 A1 | 10/2004 | Wang et al. |
| 2004/0230271 A1 | 11/2004 | Wang et al. |
| 2004/0243170 A1 | 12/2004 | Suresh et al. |
| 2004/0243220 A1 | 12/2004 | Gianotti et al. |
| 2004/0249428 A1 | 12/2004 | Wang et al. |
| 2004/0254419 A1 | 12/2004 | Wang et al. |
| 2004/0254632 A1 | 12/2004 | Alt et al. |
| 2005/0004653 A1 | 1/2005 | Gerberding et al. |
| 2005/0025797 A1 | 2/2005 | Wang et al. |
| 2005/0033407 A1 | 2/2005 | Weber et al. |
| 2005/0049480 A1 | 3/2005 | Gray |
| 2005/0049481 A1 | 3/2005 | Gray et al. |
| 2005/0049482 A1 | 3/2005 | Gray et al. |
| 2005/0049683 A1 | 3/2005 | Gray et al. |
| 2005/0049684 A1 | 3/2005 | Gray et al. |
| 2005/0049685 A1 | 3/2005 | Gray et al. |
| 2005/0049686 A1 | 3/2005 | Gray et al. |
| 2005/0049688 A1 | 3/2005 | Gray et al. |
| 2005/0049689 A1 | 3/2005 | Gray et al. |
| 2005/0065430 A1 | 3/2005 | Wiethoff et al. |
| 2005/0065437 A1 | 3/2005 | Weber et al. |
| 2005/0079132 A1 | 4/2005 | Wang et al. |
| 2005/0080459 A1 | 4/2005 | Jacobson et al. |
| 2005/0085895 A1 | 4/2005 | Brown et al. |
| 2005/0090886 A1 | 4/2005 | MacDonald et al. |
| 2005/0107870 A1 | 5/2005 | Wang et al. |
| 2005/0113669 A1 | 5/2005 | Helfer et al. |
| 2005/0113676 A1 | 5/2005 | Weiner et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0131522 A1 | 6/2005 | Stinson et al. |

| | | |
|---|---|---|
| 2005/0143651 A1 | 6/2005 | Verard et al. |
| 2005/0149002 A1 | 7/2005 | Wang et al. |
| 2005/0149157 A1 | 7/2005 | Hunter et al. |
| 2005/0149169 A1 | 7/2005 | Wang et al. |
| 2005/0152946 A1 | 7/2005 | Hunter et al. |
| 2005/0154374 A1 | 7/2005 | Hunter et al. |
| 2005/0155779 A1 | 7/2005 | Wang et al. |
| 2005/0158356 A1 | 7/2005 | Hunter et al. |
| 2005/0159661 A1 | 7/2005 | Connelly et al. |
| 2005/0165470 A1 | 7/2005 | Weber |
| 2005/0165471 A1 | 7/2005 | Wang et al. |
| 2005/0169960 A1 | 8/2005 | Hunter et al. |
| 2005/0169961 A1 | 8/2005 | Hunter et al. |
| 2005/0175664 A1 | 8/2005 | Hunter et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0178584 A1 | 8/2005 | Wang et al. |
| 2005/0181005 A1 | 8/2005 | Hunter et al. |
| 2005/0181009 A1 | 8/2005 | Hunter et al. |
| 2005/0181010 A1 | 8/2005 | Hunter et al. |
| 2005/0182450 A1 | 8/2005 | Hunter et al. |
| 2005/0182463 A1 | 8/2005 | Hunter et al. |
| 2005/0182467 A1 | 8/2005 | Hunter et al. |
| 2005/0182468 A1 | 8/2005 | Hunter et al. |
| 2005/0182469 A1 | 8/2005 | Hunter et al. |
| 2005/0183731 A1 | 8/2005 | Hunter et al. |
| 2005/0186239 A1 | 8/2005 | Hunter et al. |
| 2005/0186244 A1 | 8/2005 | Hunter et al. |
| 2005/0186245 A1 | 8/2005 | Hunter et al. |
| 2005/0187140 A1 | 8/2005 | Hunter et al. |
| 2005/0187582 A1 | 8/2005 | Weiner |
| 2005/0187600 A1 | 8/2005 | Hunter et al. |
| 2005/0192647 A1 | 9/2005 | Hunter et al. |
| 2005/0196421 A1 | 9/2005 | Hunter et al. |
| 2005/0197527 A1 | 9/2005 | Bolling |
| 2005/0208095 A1 | 9/2005 | Hunter et al. |
| 2005/0209664 A1 | 9/2005 | Hunter et al. |
| 2005/0209665 A1 | 9/2005 | Hunter et al. |
| 2005/0209666 A1 | 9/2005 | Hunter et al. |
| 2005/0215764 A1 | 9/2005 | Tuszynski et al. |
| 2005/0216075 A1 | 9/2005 | Wang et al. |

FOREIGN PATENT DOCUMENTS

| | | |
|---|---|---|
| WO | WO 03/037217 A1 | 5/2003 |
| WO | WO 2004/021927 A2 | 3/2004 |
| WO | WO 2005/039419 | 5/2005 |
| WO | WO 2005/046789 | 5/2005 |
| WO | WO 2005/092431 | 10/2005 |

OTHER PUBLICATIONS

United States Patent and Trademark Office Restriction Requirement for related U.S. Appl. No. 11/215,666 dated Jul. 13, 2007 (6 pgs.).
Applicant's Restriction Response dated Aug. 13, 2007 to Examiner's Restriction Requirement dated Jul. 13, 2007 (7 pgs.).
United States Patent and Trademark Office Office Action for related U.S. Appl. No. 11/215,666 dated Sep. 24, 2007 (23 pgs.).
Applicant's Amendment and Response dated Dec. 19, 2007 to Examiner's Office Action dated Sep. 24, 2007 (34 pgs.).
United States Patent and Trademark Office Office Action for related U.S. Appl. No. 11/215,666 dated Jun. 18, 2008 (21 pgs.).
Applicant's Amendment and Response dated Sep. 4, 2008 to Examiner's Office Action dated Jun. 18, 2008 (14 pgs.).

CARDIAC SLEEVE APPARATUS, SYSTEM AND METHOD OF USE

FIELD OF THE DISCLOSURE

This application is a continuation of U.S. application Ser. No. 11/215,666 filed Aug. 29, 2005, the specification of which is incorporated herein by reference.

BACKGROUND OF THE INVENTION

Congestive heart failure is a progressive and debilitating illness. The disease is characterized by a progressive enlargement of the heart. As the heart enlarges, it is required to perform an increasing amount of work in order to pump blood with each heartbeat. In time, the heart becomes so enlarged that it cannot adequately supply blood. An afflicted patient is fatigued, unable to perform even simple exerting tasks, and experiences pain and discomfort.

Patients suffering from congestive heart failure are commonly grouped into four classes (i.e., Classes I, II, III and IV). In the early stages (e.g., Classes I and II), drug therapy is the most commonly prescribed treatment. Drug therapy treats the symptoms of the disease and may slow the progression of the disease. Unfortunately, there is presently no cure for congestive heart failure. Even with drug therapy, the disease will progress.

One treatment for late-stage congestive heart failure is heart transplant. However, even if the patient qualifies for transplant and a heart is available for transplant, it is noted that heart transplant procedures are very risky, invasive, expensive and only shortly extend a patient's life. For example, prior to transplant, a Class IV patient may have a life expectancy of 6 months to one-year. Heart transplant may improve the expectancy to about five years. Similar risks and difficulties exist for mechanical heart transplants as well.

Another technique for the treatment for late stage congestive heart failure is a cardiomyoplasty procedure. In this procedure, the latissimus dorsi muscle (taken from the patient's shoulder) is wrapped around the heart and electrically paced synchronously with ventricular systole. Pacing of the muscle results in muscle contraction to assist the contraction of the heart during systole. However, even though cardiomyoplasty has demonstrated symptomatic improvement, studies suggest the procedure only minimally improves cardiac performance. Moreover, the procedure is highly invasive, expensive and complex, requiring harvesting a patient's muscle and an open chest approach (i.e., sternotomy) to access the heart.

Recently, a surgical procedure referred to as the Batista procedure has been developed. The procedure includes dissecting and removing portions of the heart in order to reduce heart volume. Others have used external constraints such as jackets, girdles, fabric slings or clamps to constrain and remodel the heart and reduce heart volume. See, e.g., U.S. Pat. No. 6,293,906 (citing numerous references including U.S. Pat. Nos. 5,702,343 and 5,800,528) and U.S. Pat. No. 6,095,968. In accordance with an example from the above '906 patent, a cardiac constraint device can be placed on an enlarged heart and fitted snug during diastole; for example, a knit jacket device can be loosely slipped on the heart, the material of the jacket can be gathered to adjust the device to a desired tension, and the gathered material can be sutured or otherwise fixed to maintain the tensioning.

DETAILED DESCRIPTION

Embodiments of the present invention are directed to an apparatus, system, and method for treating congestive heart failure. In addition, the embodiments of the present invention can be used in treating patients who have had an acute myocardial infarction, in addition to other causes of left ventricular failure from other diseases such as idiopathic dilated cardiomyopathy, hypertrophic cardiomyopathy, and viral cardiomyopathy.

Embodiments of the present invention include a cardiac assist sleeve that acts to apply elastic compressive reinforcement on the ventricles of the heart. Application of the elastic compressive reinforcement is believed to help reduce tension on the ventricle walls and to assist in the pumping action of the left ventricle. In addition, embodiments discussed herein allow for compressive reinforcement to be applied to the left ventricle without unduly limiting the natural volumetric changes of the left ventricle (e.g., without limiting the natural diastolic volume of the left ventricle).

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of valve. In addition, discussion of features and/or attributes for an element with respect to one FIG. can also apply to the element shown in one or more additional FIGS.

Figure 1:
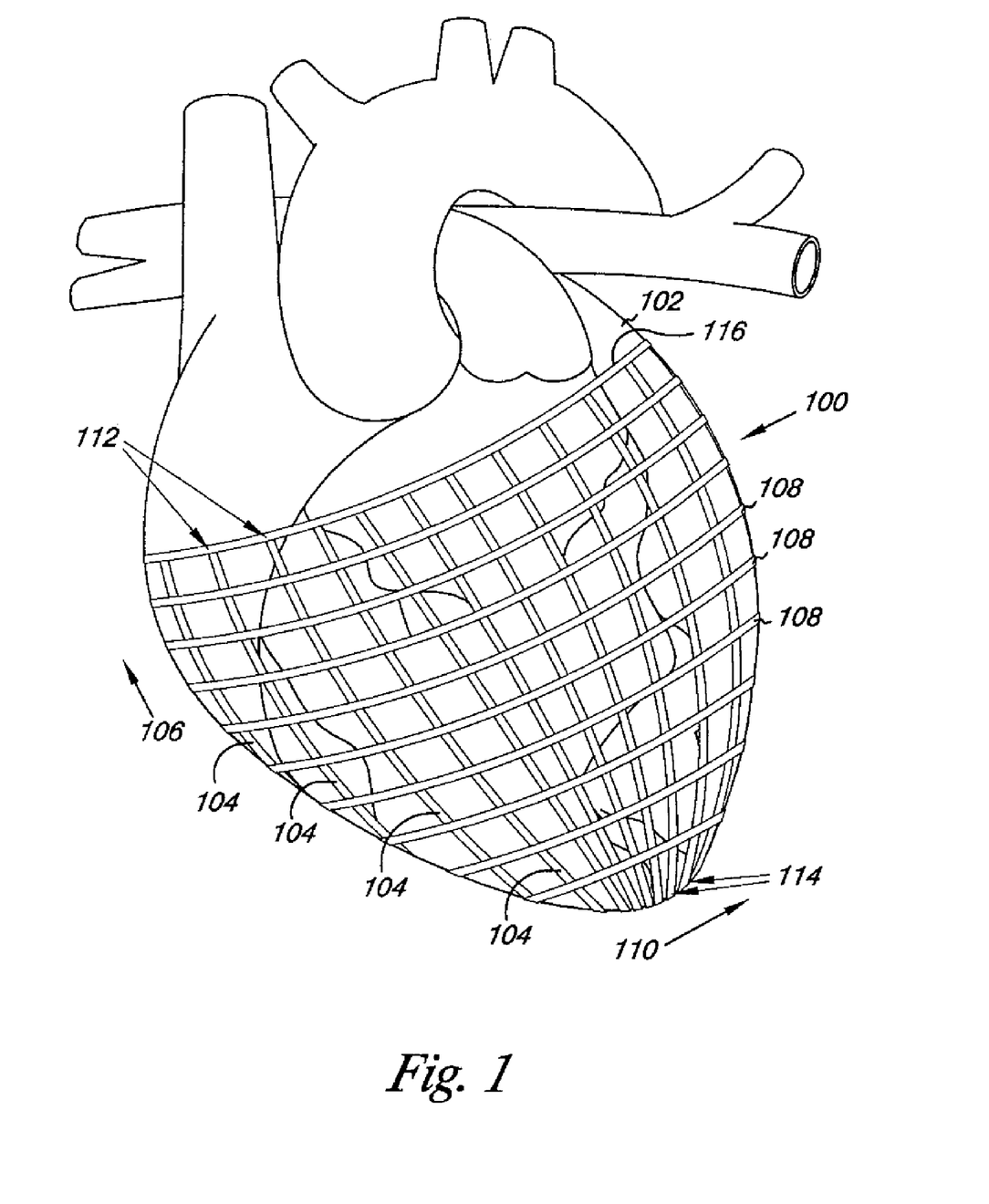
FIG. 1 illustrates an embodiment of a cardiac assist sleeve according to the present invention.
Figure 2A:
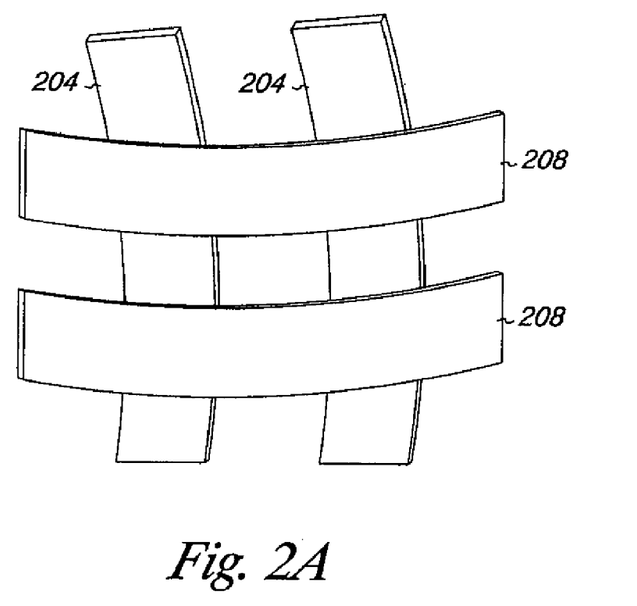
FIGS. 2A and 2B illustrate one embodiment of a segment of the cardiac assist sleeve according to the present invention.

FIG. 1 illustrates one embodiment of a cardiac assist sleeve 100 positioned over a portion of a heart 102. As illustrated, the cardiac assist sleeve 100 includes first elongate strips 104 that extend substantially in a first direction 106, and second elongate strips 108 that extend in a second direction 110. As used herein, an "elongate strips" includes elongate structures having a polygonal cross-section having perpendicular sides, one or more convex sides, or one or more concave sides. These embodiments, however, are not limited to the present examples as other cross-sectional geometries are also possible. An example can include, but is not limited to, structures having a rectangular cross-section. In addition, such structures need not have a uniform width. In other words, dimensions of the polygonal cross-section can change along the length of one or more of the elongate strips.

The first elongate strips 104 and the second elongate strips 108 of the cardiac assist sleeve 100 are configured to define a volume into which at least a portion of the heart 102 resides. As illustrated, the volume of the cardiac assist sleeve 100 can encompass a volume from approximately the A-V groove to the apex of the left ventricle. The volume of the cardiac assist sleeve 100 reversibly changes during the cardiac cycle of the heart 102 to apply elastic compressive reinforcement on the ventricles of the heart 102. In one embodiment, this change in volume is imparted to the cardiac assist sleeve 100 due to the configuration and the materials used in the first elongate strips 104 and the second elongate strips 108 of the cardiac assist sleeve 100.

In one embodiment, the first elongate strips 104 are formed of a first shape-memory alloy and the second elongate strips 108 are formed of a second shape-memory alloy. As used herein, a "shape-memory alloy" includes those metals that have a predetermined geometry (i.e., shape) to which the structure made from the metal returns after being elastically deformed. The shape memory alloys can include, but are not limited to, those that return to its predetermined geometry due to thermal energy (i.e., temperature), such as Nitinol, and/or the influence of a magnetic field. Other examples of shape memory alloys include those composed of titanium-palladuim-nickel, nickel-titanium-copper, gold-cadmium, iron-zinc-copper-aluminum, titanium-niobium-aluminum, hafnium-titanium-nickel, iron-manganese-silicon, nickel-titanium, nickel-iron-zinc-aluminum, copper-aluminum-iron, titanium-niobium, zirconium-copper-zinc, and nickel-zirconium-titanium. Other metal and metal alloys are also possible.

As illustrated, the second elongate strips 108 intersect and pass the first elongate strips 104 in the second direction. The first and second elongate strips 104 and 108 can include individual elongate strips that are associated with each other so as to form the cardiac assist sleeve 100. Alternatively, the first and second elongate strips 104 and 108 can be formed from one or more sheets of the shape memory alloy that are processed to provide the strips 104 and 108. In one embodiment, the first elongate strips and the second elongate strips have a thickness of 10 to 200 microns.

For example, individual elongate strips can be shaped (e.g., cut), arranged, and joined to form the cardiac assist sleeve 100. Shaping of the individual elongate strips can be accomplished by laser cutting, water jet cutting, electron discharge machine, and/or other cutting methods as are known or will be known.

The strips can then be arranged on a template (e.g., a model) of a heart. In one embodiment, the template can be of the patient's heart that is to receive the resulting cardiac assist sleeve 100.

The elongate strips can then be joined at one or more predetermined locations through chemical and/or mechanical joining. For example, predetermined locations of the elongate strips can be bonded to each other through the use of adhesives (e.g., chemical adhesives) and/or laser welding. Other joining techniques are also possible. As will be appreciated, the strips need not be secured and/or joined at every location where they intersect.

In an alternative embodiment, the strips 104 and 108 of the cardiac assist sleeve 100 can be formed from one or more sheets of the shape memory alloy. As used herein, a sheet of the shape memory alloy can include those formed from calendaring techniques, film forming techniques (e.g., photochemical etching), or sputter coating techniques. For example, the strips 104 and 108 can be formed as a thin film in a sputter coating process. A useful sputter coating process can include those described in U.S. Pat. No. 6,533,905 to Johnson et al. entitled "Method for Sputtering TiNi Shape-Memory Alloys," which is incorporated herein by reference in its entirety.

The shape memory alloy noted herein may be used in conjunction with radioopaque filler materials such as barium sulfate, bismuth trioxide, bismuth carbonate, powdered tungsten, powdered tantalum, or the like so that the location of the sleeve 100 may be radiographically visualized within the human body. In addition, therapeutic agent(s) can be applied to the surfaces of the strips 104 and 108. The variety of different therapeutic agents that can be used include, without limitation: antiinfectives such as antibiotics and antiviral agents; analgesics and analgesic combinations; anti-inflammatory agents; hormones such as steroids; and naturally derived or genetically engineered proteins, polysaccharides, glycoproteins, or lipoproteins, anti-thrombotic agents, anti Pt agents, anti-immunogenic agents, anti-mitotic agents, anti proliferative agents, and angiogenic agents.

As discussed herein, the volume of the cardiac assist sleeve 100 changes during the cardiac cycle of the heart 102 to apply elastic compressive reinforcement on the ventricles of the heart 102. In one embodiment this change in volume results from reversible changes in the shape of at least one of the first elongate strips 104 and/or the second elongate strips 108.

Figure 2B:
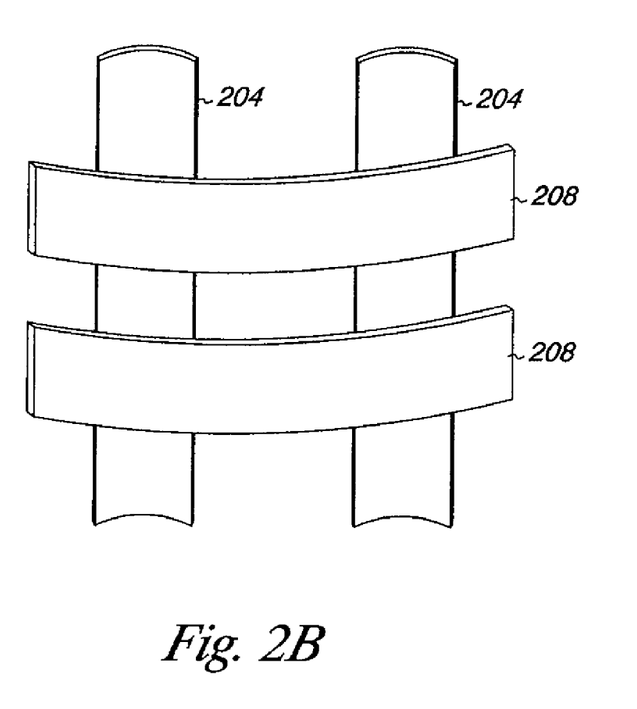

Examples of changes to the first and second elongate strips are illustrated in FIGS. 2A-2B and 3A-3B. FIGS. 2A and 2B illustrate segments of the first and second elongate strips 204 and 208 in which the first elongate strips 204 change shape to reversibly change the volume of the cardiac assist sleeve. As illustrated, the first elongate strips 204 include a cross-sectional shape across the first direction that reversibly changes between a flat cross-sectional shape and a curved cross-sectional shape to change the volume of the cardiac assist sleeve.

In one embodiment, the length of strips 208 do not significantly change, so as strips 204 curve, they reduce the volume of the sleeve. As the heart fills during diastole the curves in strips 204 are elastically deformed (i.e., compressed so as to flattened) to look like those in FIG. 2A. Elasticity refers to the ability of a material or object to deform and recover its shape when a load is first applied and then removed. In its deformed state, the strips 204 can store potential energy that is released as the heart starts into systole. Strips 204 would have to attach (if at all) to strips 208 so as to not constrain the curving of strips 204. For example, strips 204 could be attached at its outer edge to strips 208.

As will be appreciated, the number of curves (density), their shape (e.g., U-shaped, V-shaped, teardrop-shaped, keyhole-shaped), direction, material dimensions (e.g., thickness) of the strip 204 can be varied to modify the stiffness and the elasticity of the sleeve 200. In addition, it is possible to modify one or more of these variables on one or more of the strips to provide selective elastic resistance (e.g., stiffness) in different areas of the sleeve 200. For example, it would be possible to make the sleeve 200 stiffer in the area surrounding the left ventricle as compared to the area surrounding the right ventricle.

Figure 3A:
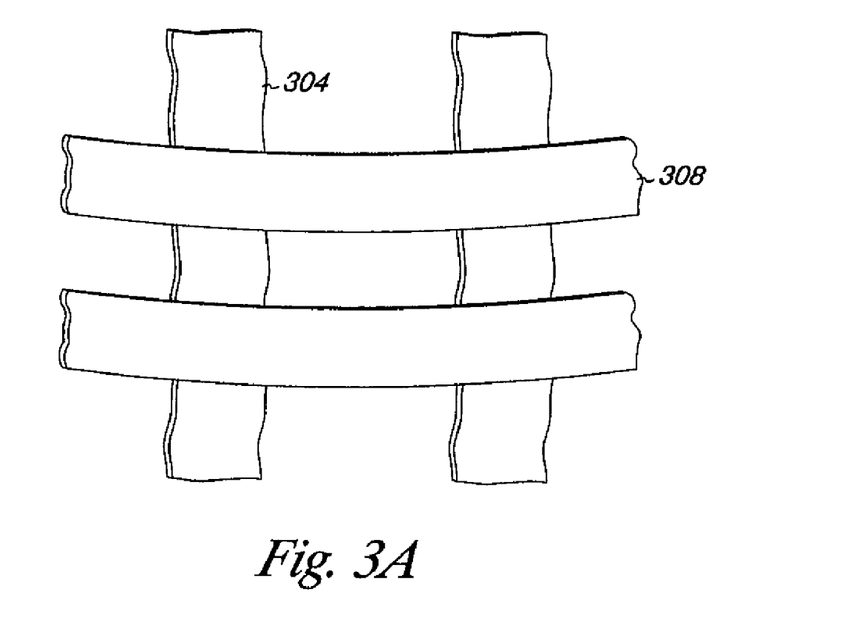
FIGS. 3A and 3B illustrate one embodiment of a segment of the cardiac assist sleeve according to the present invention.
Figure 3B:
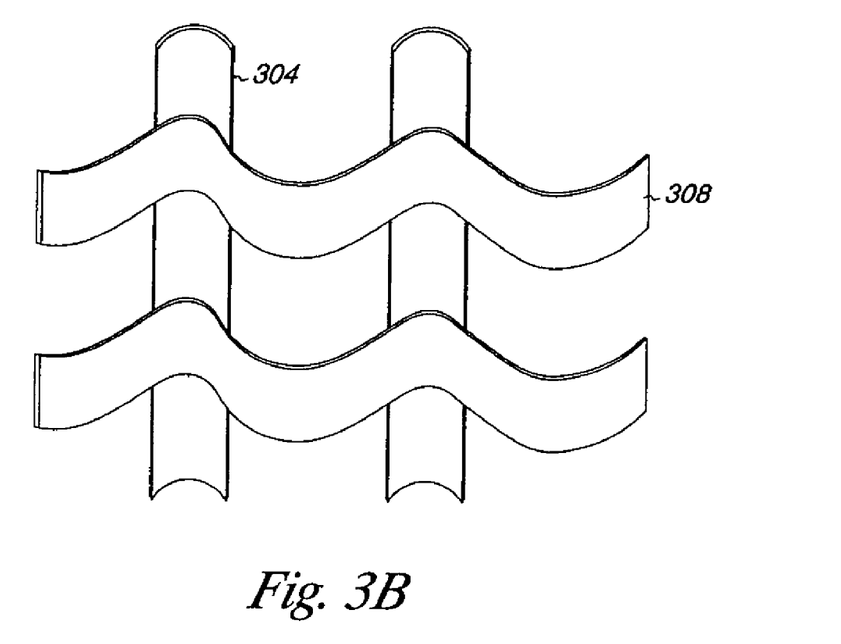

FIGS. 3A and 3B provide an additional embodiment of changes that can occur to the first and second elongate strips so as to change volume of the sleeve. In the present example, both the strips 204 and 208 can change shape to provide reversible changes to the volume of the sleeve. In FIG. 3A, the strips 304 can change shape as discussed herein with respect to FIGS. 2A and 2B. The second elongate strips 308 include a cross-sectional shape taken along the second direction that reversibly changes between a flat cross-sectional shape (illustrated in FIG. 3A) and a non-flat cross-sectional shape (illustrated in FIG. 3B) to change the volume of the cardiac assist sleeve.

As illustrated, the second elongate strips 308 can have a curving (e.g., sinusoidal shape) geometric shape along the second direction. As the heart fills during diastole the curves in 304 and 308 are compressed (flattened) to look like those in 3A. There is potential energy stored in the flattened strips 304 and 308 that is released as the heart starts into systole. Strips 304 would have to attach (if at all) to strips 308 so as to not constrain the curving of strips 304 and 308. For example, strips 304 can be attached at their outer edge to strips 308. Alternatively, strips can be attached along their face, where the curves in strips 304 and 308 are configured to bend in the same direction and to the same extent (the bends in each mirror each other).

The configurations of the strips in the sleeve also allow for volume changes to occur primarily circumferentially around the left ventricle of the heart as apposed to linearly along the central axis of the left ventricle. In one embodiment, this is because changes to the shape of the first strips occur to the cross-sectional shape of the strips, where as changes to the shape of the second strips occur to the elongate shape of the strips.

Referring again to FIG. 1, each of the first elongate strips 104 includes a first end 112 and a second end 114. In one embodiment, the first end 112 of the strips 104 are joined at a collar 116. In one embodiment, the collar is where the ends of strips 104 are joined at set locations. Set locations can be radially symmetrical (e.g., equally spaced) around an axis extending in the first direction, but do not have to be. Collar could also include anchors (e.g., staples) or locations for sutures to be used to secure the sleeve to the heart. Two or more of the second ends 114 can further be joined at a common location. In one embodiment, this allows the relative positions of the first elongate strips 104 to be maintained.

Figure 4A:
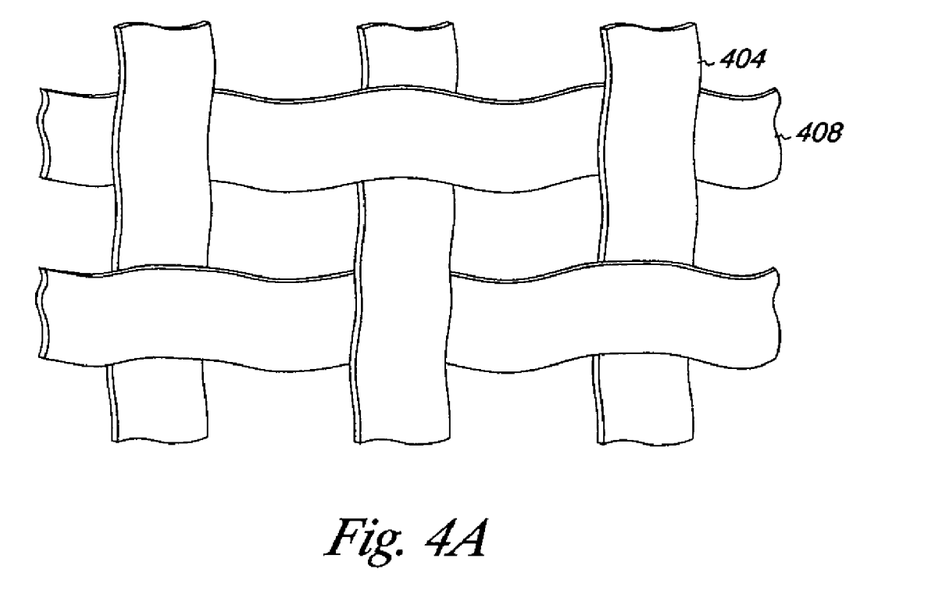
FIGS. 4A and 4B illustrate one embodiment of a segment of the cardiac assist sleeve according to the present invention.
Figure 4B:
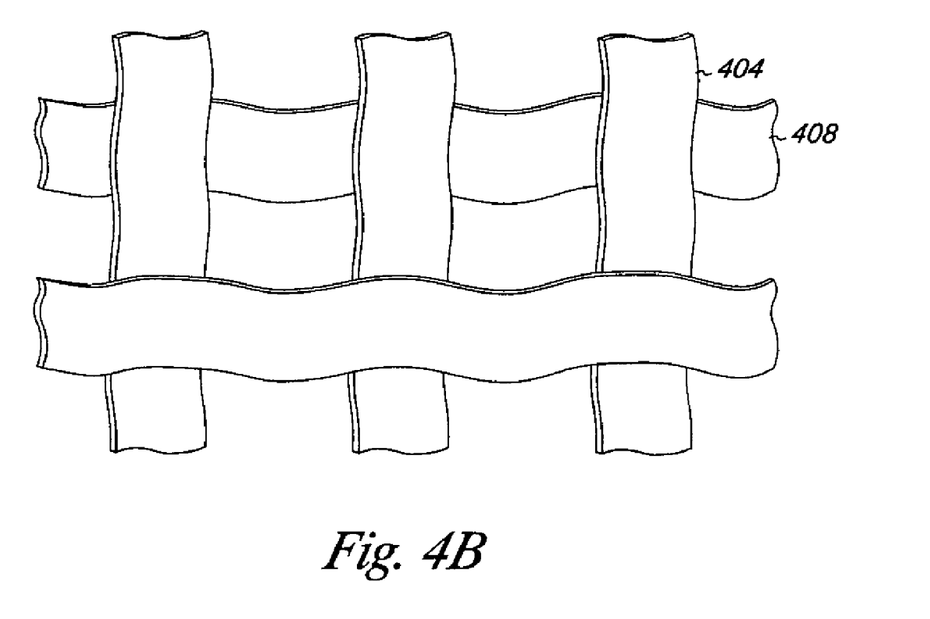

As will be appreciated, the strips 104 and 108 can intersect and pass each other in a number of different configurations. For example, as illustrated in FIGS. 4A and 4B, the strips 404 and 408 can have a woven configuration. As illustrated in FIG. 4A, each of the first strip 404 and the second strip 408 alternate passing over and then under each other (e.g., a basket weave pattern). As illustrated in FIG. 4B, the first strips 404 can pass over and then under each of the second strips 408. Other weaving patterns are possible, including braiding of the first and second strips.

Strips can also be actuated when a potential and/or heat is applied to the strip. For example, when electrical potential or heat is applied to the strip in the stressed state (compressed states as illustrated in FIGS. 2A and 3A), the resistive force generated by the bending deformation increases. In essence, the strip can generate a contractile force when potential is applied to the strip. So, it is possible to actively power an otherwise passive elastic strip in order to achieve systolic pumping assistance.

Strips can also have a laminate structure that allows at least one layer of the strip to be actuated when an electrical potential and/or beat is applied to the strip. For example, first elongate strips can include a cladding of the first shape-memory alloy and a third shape-memory alloy, the first shape-memory alloy and the third shape-memory alloy each having at least one layer that extends in the first direction. In one embodiment, the first and third memory metal can be Nitinol that has had their respective geometries set at different temperatures.

As will be appreciated, elastically deforming the strips can provide for the actuator design that employs at least a bi-metal sandwich technology such that a spring element is biased against a contractile one-way shape memory effect of the memory metal (e.g., nitinol). This allows the strips to restore more fully to full strain recovery after each cycle.

In the present example, the first shape-memory alloy of the cladding can be actuated by the application of the electrical potential and/or heat to change its shape. This feature could be combined with the third shape-memory alloy that is conditioned to bend in the opposing direction of the first shape-memory alloy of the cladding to allow for work to be acquired from the strip as is moves through its full range of motion.

Figure 5A:
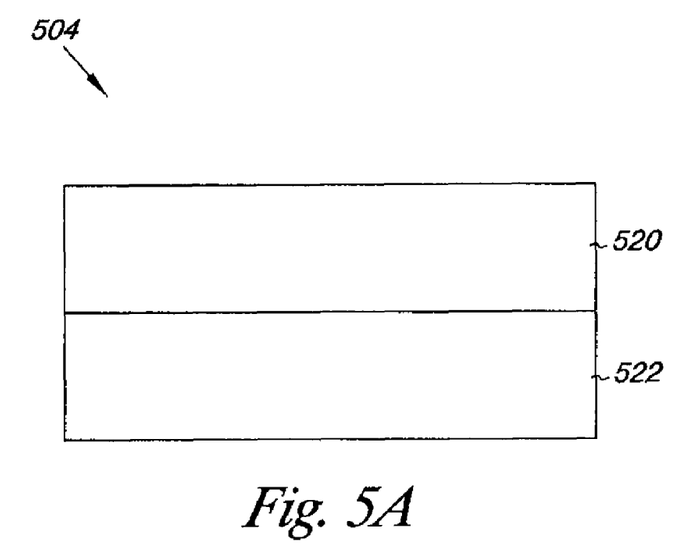
FIGS. 5A and 5B illustrate embodiments of a strip of the cardiac assist sleeve according to the present invention.
Figure 5B:
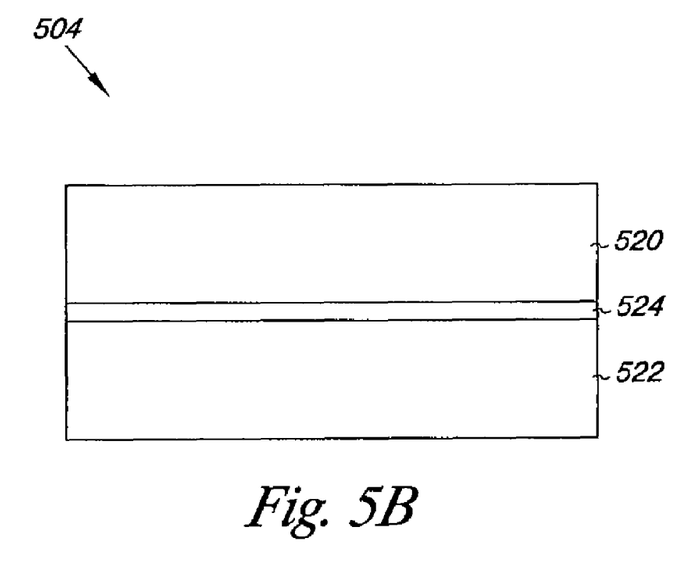

FIGS. 5A and 5B provide an illustration of a first strip 504 having the cladding (i.e., a sandwich) construction. As illustrated, first strip 504 includes a first layer 520 of the first shape-memory alloy and a second layer 522 of the third shape-memory alloy. FIG. 5B provides an illustration where a thermal and/or electrically insulating layer 524 is provided between layers 520 and 522. As will be appreciated, this same structure for the first strip 504 can be applied to the second strip discussed herein.

Figure 6A:
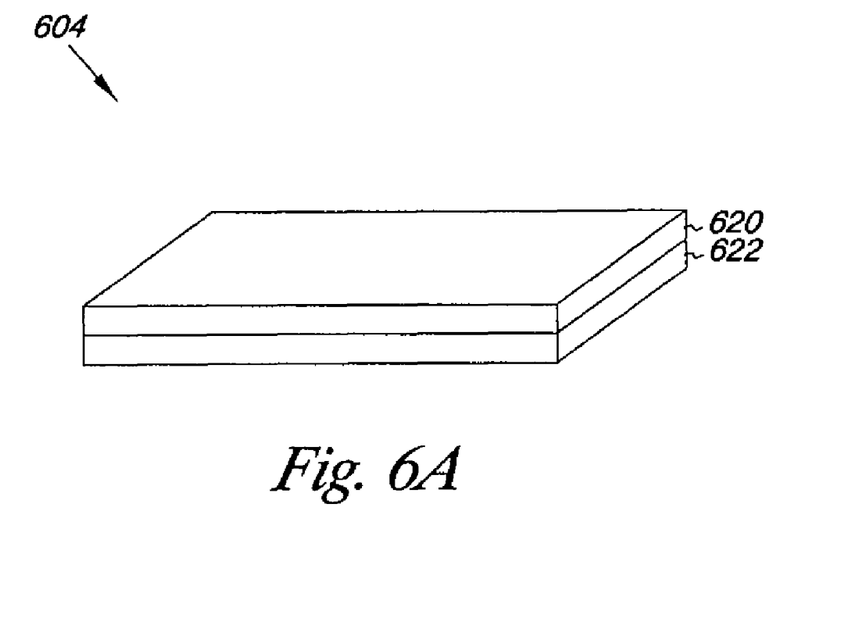
FIGS. 6A and 6B illustrate one embodiment of a strip of the cardiac assist sleeve according to the present invention.
Figure 6B:
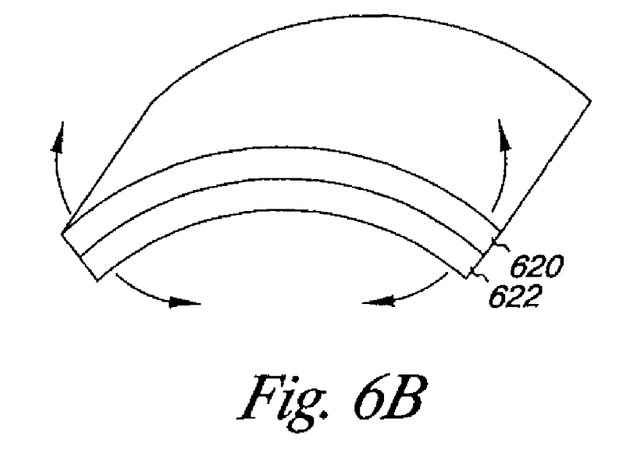

FIGS. 6A and 6B illustrate an embodiment in which a potential is applied to strip 604 having layers 620 and 622. FIG. 6A has layer 620 in its set geometric shape, whereas layer 622 is under tension. When electrical potential or heat is applied to layer 622 it is actuated to bend as illustrated in FIG. 6B. Upon bending, layer 620, acting as a spring element, deviates from its set geometric shape. When the potential is removed, the tension load in layer 620 returns the strip 604 to is configuration in FIG. 6A. This allows for work to be done in both directions as the strip 604 moves. So, a sleeve made with this strip configuration (when properly coupled to the heart) can provide assistance to the heart in both diastole and systole.

The sleeve illustrated in the present embodiments not only has the capability of acting as a passive restraint around the heart, but may also be actively powered to provide contractile assistance during systole and/or diastole. This may be done by the application of electrical potential to the sleeve.

Figure 7:
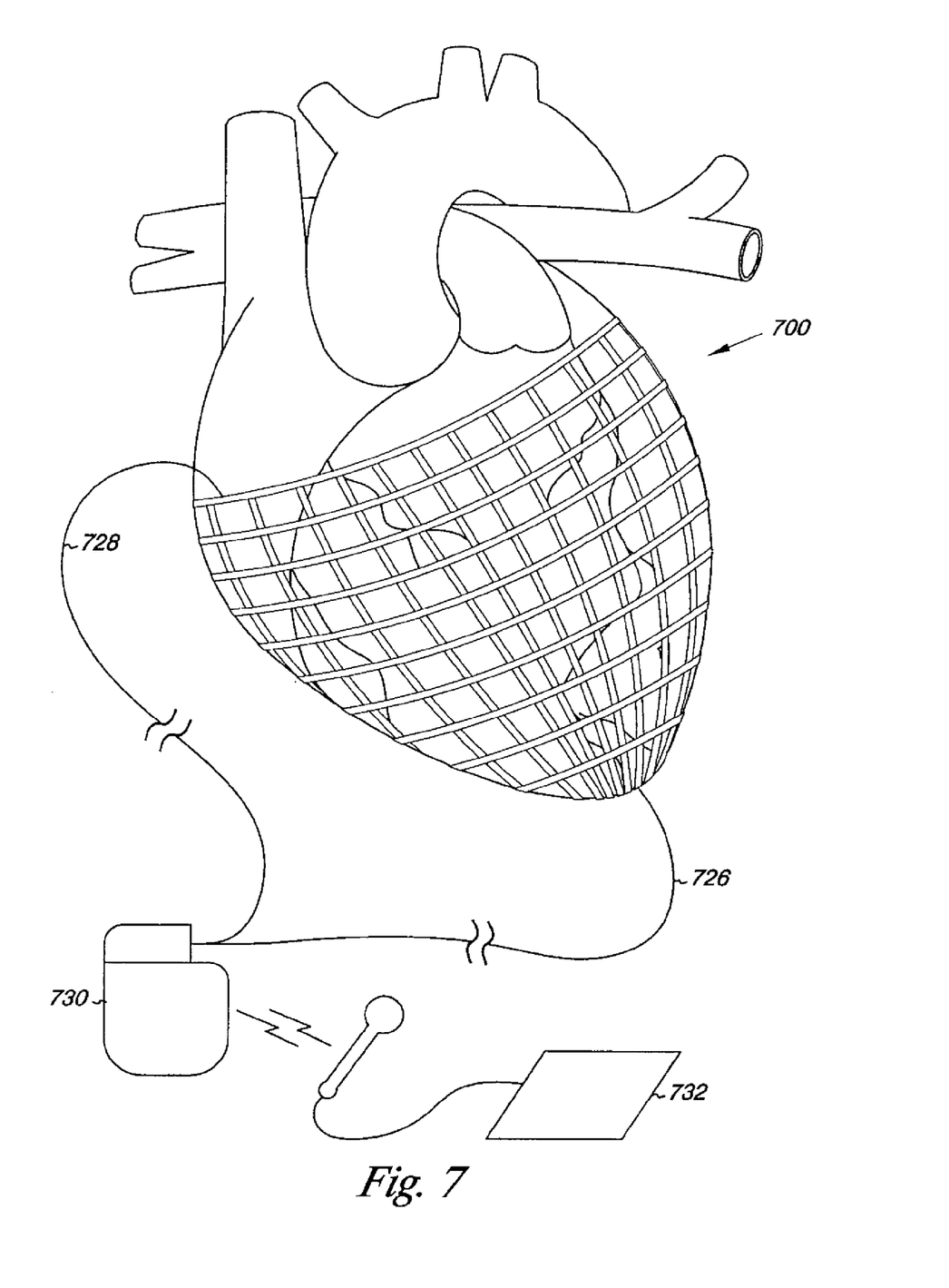
FIG. 7 illustrates an embodiment of a cardiac assist sleeve according to the present invention.

FIG. 7 provides an illustration in which the sleeve 700 is coupled to leads 726 and 728 and a potential generator 730. Potential generator 730 includes a battery and circuitry for sensing portions of the cardiac cycle so as to more properly time the contractile assistance and to communicate via wireless (e.g., RF) with an external programmer 732.

The entire sleeve 700 can be configured to be actuated by the potential generator 730, and/or select portions of the sleeve 700. For example, in one embodiment just the first strips can be actuated during systole. Other combinations can be envisioned.

In another embodiment, the potential generator 730 can be used to modify the compliance/stiffness of the strips by applying different levels of electrical potential. As such, the potential is not used to actively "squeeze" the heart during systole, but rather to provide for adjustable compliance of the sleeve. This allows for adjustments in the amount of resistive pressure the sleeve exerts on the left ventricle during both systole and diastole. The passive stiffness of the sleeve can be set to change throughout the cardiac cycle, or it can be adjusted to maintain constant levels.

As will be appreciated, the sleeve 700 may be integrated with an implantable pacemaker or an internal cardiac defibrillator, according to the needs of the patient.

In addition, embodiments of the sleeve can also be utilized inside the LV chamber.

In one embodiment, the sleeve can be delivered through conventional cardiothoracic surgical techniques through a median sternotomy. Alternatively, the sleeve can be delivered through minimally invasive surgical access to the thoracic cavity. Such a minimally invasive procedure can be accomplished on a beating heart, without the use of cardiopulmonary bypass. Access to the heart can be created with conventional surgical approaches.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method of forming a cardiac assist sleeve, comprising:
arranging first elongate strips of a first shape-memory alloy, the first elongate strips having a cross-sectional shape taken perpendicularly across a lengthwise line of symmetry;
arranging second elongate strips of a second shape-memory alloy to intersect and pass the first elongate strips, where the first elongate strips and the second elongate strips define a volume that changes as the cross-sectional shape of the first elongate strips reversibly change between a first cross-sectional shape having flat surfaces and a second cross-sectional shape having one convex surface and one concave surface opposite the convex surface to change the volume of the cardiac assist sleeve; and
securing a first end of the first elongate strips around a collar.

2. The method of claim 1, including forming the first elongate strips and the second elongate strips in a sputter coating operation.

3. The method of claim 2, including cladding a third shape memory alloy to the first elongate strips and the second elongate strips.

4. The method of claim 3, including depositing an electrically insulating layer between the first shape-memory alloy and the third shape-memory alloy.

5. The method of claim 1, including imparting a first shape into the first shape-memory alloy of the first elongate strips.

6. The method of claim 1, including imparting a second shape into the second shape-memory alloy of the second elongate strips.

7. The method of claim 1, including joining a second end of the first elongate strips at a common location.

8. The method of claim 1, where arranging the second elongate strips to intersect and pass the first elongate strips includes weaving the first elongate strips and the second elongate strips.

9. A method of using a cardiac assistance device, comprising:
positioning a cardiac assist sleeve adjacent a left ventricle of a heart, where the cardiac assist sleeve includes:
first elongate strips of a first shape-memory alloy, the first elongate strips having a cross-sectional shape taken perpendicularly across a lengthwise line of symmetry; and
second elongate strips of a second shape-memory alloy that intersect and pass the first elongate strips, the first elongate strips and the second elongate strips define a volume to receive the left ventricle of the heart;
securing a portion of the cardiac assist sleeve to the heart; and
assisting the left ventricle of the heart by reversibly changing the cross-sectional shape of at least one of the first elongate strips between a first cross-sectional shape having perpendicular sides and a second cross-sectional shape having one convex surface and on concave surface opposite the convex surface to change the volume of the cardiac assist sleeve.

10. The method of claim 9, where producing reversible changes in the cross-sectional shape includes applying an electrical potential across the first shape-memory alloy and the second shape-memory alloy to produce the changes in the cross-sectional shape.

11. The method of claim 10, where applying the electrical potential is synchronized with predetermined portions of a contraction cycle of the heart.

12. The method of claim 9, where securing a portion of the cardiac assist sleeve to the heart includes wrapping the cardiac assist sleeve around at least a portion of the heart, where at least a portion of the cardiac assist sleeve freely overlaps adjacent the portion of the cardiac assist sleeve secured to the heart.

* * * * *